(12) United States Patent
Myerson et al.

(10) Patent No.: US 7,122,642 B2
(45) Date of Patent: Oct. 17, 2006

(54) METHOD FOR PRODUCING CRYSTAL POLYMORPHS AND CRYSTAL POLYMORPHS PRODUCED THEREBY

(75) Inventors: Allan S. Myerson, Chicago, IL (US); Bruce A. Garetz, New York, NY (US)

(73) Assignee: Polytechnic University, Brooklyn, NY (US)

( * ) Notice: Subject to any disclaimer, the term of this patent is extended or adjusted under 35 U.S.C. 154(b) by 0 days.

(21) Appl. No.: 10/056,490

(22) Filed: Jan. 24, 2002

(65) Prior Publication Data

US 2002/0137902 A1 Sep. 26, 2002

Related U.S. Application Data

(63) Continuation-in-part of application No. 09/694,404, filed on Oct. 23, 2000, now Pat. No. 6,426,406, which is a continuation-in-part of application No. 09/348,200, filed on Jul. 6, 1999, now abandoned.

(51) Int. Cl.
*B01D 9/02* (2006.01)
*C07K 1/30* (2006.01)

(52) U.S. Cl. ............... 530/418; 23/295 R; 204/157.15; 204/157.41; 204/157.61; 204/157.68; 204/157.69; 204/157.75; 204/157.82; 204/157.87; 204/157.9; 204/158.14; 530/427; 562/575

(58) Field of Classification Search ............... 23/295 R; 562/575; 530/418, 427; 204/157.15, 157.41, 204/157.61, 157.68, 157.69, 157.75, 157.82, 204/157.87, 157.9, 158.14
See application file for complete search history.

(56) References Cited

U.S. PATENT DOCUMENTS

| 5,976,325 | A | | 11/1999 | Blanks ................. 204/157.41 |
| 6,426,406 | B1 | * | 7/2002 | Myerson et al. ............ 530/418 |
| 6,596,077 | B1 | * | 7/2003 | Myerson ...................... 117/68 |
| 2003/0024470 | A1 | * | 2/2003 | Myerson ...................... 117/68 |
| 2003/0044433 | A1 | * | 3/2003 | Werling et al. ............. 424/400 |
| 2003/0101926 | A1 | * | 6/2003 | Myerson ...................... 117/84 |

OTHER PUBLICATIONS

Zaccaro et al. Nonphotochemical, Laser–Induced Nucleation of Sueprsaturated Aqueous Glycine Produces Unexpected gamma–Polymorph. Crystal Growth & Design. vol. 1, No. 1, pp. 5–8 (Nov. 1, 2000).*

The Merck Index, Eleventh Ed. Rahway: Merck & Co., Inc., pp. 57, 1553 (1989).*

Garetz et al., Nonphotochemical, Polarization–Dependent Laser–Induced Nucleation in Supersaturated Aqueous Urea Solutions, Physical Review Letters, vol. 77, No. 16, pp. 3475–3476 (Oct. 14, 1996).

* cited by examiner

*Primary Examiner*—Jeffrey Edwin Russel
(74) *Attorney, Agent, or Firm*—Laurence P. Colton; Powell Goldstein LLP

(57) ABSTRACT

A method to prepare new or unexpected polymorphs of materials which have not been observed, or to obtain a known polymorph under different conditions than those in which it is usually made, by using a laser to cause nucleation and crystal growth to occur in a supersaturated solution in such a way as to obtain a crystal structure which would not normally appear without the use of the laser.

6 Claims, 6 Drawing Sheets

METHOD FOR PRODUCING CRYSTAL POLYMORPHS AND CRYSTAL POLYMORPHS PRODUCED THEREBY

CROSS-REFERENCE TO RELATED APPLICATION

The present application is a continuation-in-part of U.S. patent application Ser. No. 09/694,404, filed on 23 Oct. 2000, which issued as U.S. Pat. No. 6,426,406 on 30 Jul. 2002, which is a continuation-in-part of U.S. patent application Ser. No. 09/348,200, filed on 6 Jul. 1999, abandoned.

BACKGROUND

1. Technical Field

This invention relates generally to the field of inducing the nucleation of selected crystal polymorphs from supersaturated solutions and specifically to a process of inducing the nucleation of selected crystal polymorphs from supersaturated solutions by using laser light to induce nucleation.

2. Prior Art

The crystal structure of a material determined by x-ray diffraction gives a complete picture of the arrangement of the atoms (or molecules) of the chemical species in the crystalline state. It is possible, however, for a given chemical species to have the ability to crystallize into more than one internally distinct structure. This ability is called polymorphism (or allotropism if the species is an element). Different polymorphs of the same material can display significant changes in their properties as well as in their structure.

The term "polymorphism" is contrasted with "morphology." Crystals are solids with the atoms, molecules, or ions in a regular repeating structure. The overall external form is referred to as crystal morphology. The term morphology refers to the external shape of the crystal and the planes present, without reference to the internal structure. Crystals obtained experimentally can display different morphology based on different conditions, such as, for example, growth rate, stirring, and the presence of impurities. In contrast, as stated above, polymorphism refers to the internal alignment and orientation of the molecules. A substance can have several distinct polymorphs and only one morphology, or several distinct morphologies for only one polymorph. Just because the morphology changes does not mean there is a new polymorph, and vice versa. Unlike with different morphologies, one cannot tell by visual observation whether one has a different polymorph.

The prior art produces a substance with a known morphology and crystal structure. It does not produce a substance of unknown crystal structure (a new polymorph) or of unexpected structure (a known polymorph that would not normally occur under these conditions). As discussed above, there is an important distinction between morphology and polymorphism. Morphology is the external appearance of the crystal. In contrast, polymorphism refers to the internal structure of the crystal. It is important to note that crystals of a given substance with different morphologies have the same physical properties (such as melting point, solubility, electrical conductivity, etc) while different polymorphs of the same substance have different properties (e.g., diamond and graphite, which are different polymorphs of carbon).

Polymorphism is quite common in the elements and in inorganic and organic compounds and results in property changes. A dramatic example is carbon, which can crystallize as graphite or as diamond. Diamond is a cubic crystal, whereas graphite is hexagonal. In addition, properties such as hardness, density, shape, vapor pressure, dissolution rate, and electrical conductivity are all quite different for these two solids. These major differences in the properties of two polymorphs are not unique to carbon and can occur in all materials that display polymorphism. Many of the early identifications of polymorphs were minerals, such as calcium carbonate, which has three polymorphs (calcite, aragonite, and vaterite) and zinc sulfide, which has three polymorphs (wurtzite, sphalerite, and matraite). Some well known species have large numbers of polymorphs, for example water, which has eight different solid forms of ice. Organic molecular crystals often have multiple polymorphs that can be of great significance in the pharmaceutical, dye and explosives industries.

Under a given set of conditions, one polymorph is the thermodynamically stable form. This does not mean, however, that other polymorphs cannot exist or form at these conditions, only that one polymorph is stable and other polymorphs present can transform to the stable form. An example of this can be seen in heating (or cooling) a crystalline material with multiple polymorphs. As the temperature changes, the material will eventually enter a region where another polymorph is the stable form. The transformation of one polymorph to another, however, will occur at some rate that may be rapid or very slow. The transformation rate varies because the rate of transition of polymorphs depends on the type of structural changes that are involved.

Transformations can be categorized by the types of structural changes involved, which can roughly be related to the rate of transformation. For example, a transformation in which the lattice network is bent but not broken can be rapid. This type of transformation is known as displacive transformation of secondary coordination. Another type of rapid transformation can involve the breakage of weaker bonds in the crystal structure with the stronger bonds remaining in place. This is then followed by the rotation of parts of the molecule about the structure and the formation of new bonds. This type of transformation is a rotational disorder transformation. Slow transformations usually involve the breakage of the lattice network and major changes in the structure or type of bonding.

Polymorphic transformations can also be classified as first- or second-order transitions. In a first-order transition, the free energies of the two forms become equal at a definite transition temperature, and the physical properties of the crystal undergo significant changes upon transition. In a second-order transition, there is a relatively small change in the crystal lattice, and the two polymorphic forms will be similar. There is no abrupt transition point in a second order transition, although the heat capacity rises to a maximum at a second order transition point.

When a material is crystallized from solution, the transition between polymorphs can occur at a much higher rate because the transition is mediated by the solution phase. Polymorphs of a given material will have different solubilities at a given temperature, with the more stable material having a lower solubility (and a higher melting point) than the less stable polymorph. If two polymorphs are in a saturated solution, the less stable polymorph will dissolve and the more stable polymorph will grow until the transition is complete. The rate of the transition is a function of the difference in the solubility of the two forms and the overall degree of solubility of the compounds in solution. This transition requires that some amount of the stable polymorph be present, meaning that the stable polymorph must nucleate at least one crystal for the transition to begin. If a slurry of solution and crystals of a polymorph stable at a high temperature is cooled to a lower temperature, where another polymorph is the stable phase, the transition of the crystals already present will depend on the presence of nuclei of the new stable phase. The more of these nuclei present, the faster the transition will occur.

It is often possible to crystallize a metastable polymorph by applying a large supersaturation (for example rapid cooling) so that crystals of the metastable form appear before crystals of the stable form. When this occurs, if the solid is removed from the solution rapidly and dried, it is possible to obtain samples of a metastable polymorph that will not easily transform to the stable phase unless heated. If the crystals of the metastable polymorph are left in solution for any length of time, they will likely transform to the stable form by going through the solution phase. If seeds of the stable polymorph are added to the solution, the transition will occur more rapidly. At first-order phase-transition temperatures, the solubility of the two forms will be equal and both can exist.

When a material that displays polymorphism is crystallized, a metastable phase often appears first and then transforms into a stable form. This observation is summarized by Ostwald's step rule, which is also known as the Law of Successive Reactions. This law states that, in any process, the state that is initially obtained is not the most stable state but the least stable state that is closest, in terms of free-energy change, to the original state. In a crystallization process, therefore, it is possible to envision the phase transformation first occurring into the least stable polymorph (or even an amorphous phase), which transforms through a series of stages to successively more stable forms until the equilibrium form is obtained. While Ostwald's law has been observed in a wide variety of systems, it is most likely to be seen in organic molecular crystals.

Another interesting feature of organic molecular crystals is that the molecular conformation of a species can be different in two polymorphs of the same material. By molecular conformation, we are referring to the shape of the molecule. The same molecule can display different shapes (conformations by rotations about single bonds for example. Conformational polymorphism is the existence of polymorphs of the same substance in which the molecules present are in different conformations.

It is known that by subjecting some supersaturated solutions to laser light, the onset of nucleation occurs. Prior to nucleation, the supersaturated solution contains "clusters" of molecules that are not arranged in the lattice structure of a crystal. The laser light helps to align or organize the molecules in the clusters into a lattice arrangement resulting in the formation of nuclei and, after time, crystals. For a urea solution, it was shown that the laser could induce nucleation and the one and only known and expected polymorph for urea was obtained. Garetz, B. A. et al., Nonphotochemical, Polarization-Dependent, Laser-Induced Nucleation in Supersaturated Aqueous Urea Solutions, *Physical Review Letters*, Vol. 77, No. 16, pp. 3475–6 (1996).

The Garetz article does not disclose the creation of different, unexpected polymorphs or that different, unexpected polymorphs could be created using laser induced nucleation, as disclosed and claimed in the present patent application. More specifically, the Garetz adicle discloses the effect laser-induced nucleation has on the orientation of the molecules. Specifically, the Garetz article discloses that the polarization dependence of the crystallite orientation is consistent with a mechanism in which the electric field of the light plays a major role and that urea molecules are being aligned by the applied optical field, just as they are in the optical Kerr effect, also known as light-induced birefringence. The Garetz article further discloses that only urea's anisotropic polarizability is responsible for electrio-field-induced alignment at optical frequencies, thus, according to the Garetz mechanism, urea molecules in a cluster will tend to align with their $C_2$ axes parallel to an applied electric field, E, growing into a crystallite with the needle axis parallel to E.

The discovery published in the Garetz article is a photo-physical phenomenon in which the laser induced crystallization of urea causes the alignment of the urea molecules by the applied optical field. The crystals that result from the experimentation disclosed in the Garetz article were known and expected crystals. The novelty of the Garetz article is that the laser light causes the urea molecules to align, facilitating the nucleation into the known crystals. This is substantially different from the invention disclosed and claimed in the present patent application, which is the creation of different polymorphs not normally obtained using current art nucleation methods.

An application of the Garetz et al principles is in U.S. Pat. No. 5,976,325 to Blanks that discloses a method for producing a substance with a known morphology and crystal structure in aluminate solution. Blanks '325 discloses a self-seeding processes to obtain the most stable crystal structure of sodium aluminate from a supersaturated aluminate solution (i.e. Bayer Process solution) and does not implicate the polymorphism of the substance. More distinctively, the process in Blanks '325 is primarily for destroying impurities in the solution, and the light used is absorbed by the materials. Blanks '325 discloses a process for forming a precipitated alumina hydrate, comprising the steps of providing a sodium aluminate solution; and illuminating said sodium aluminate solution with light wave energy produced by the near infrared wavelength, linearly polarized output of a laser to form a precipitated alumina hydrate where no external seed is added. Much like the Garetz article, Blanks '325 discloses a method for obtaining a known crystal in a process for forming a precipitated alumina hydrate such as aluminum trihydroxide by providing a supersaturated sodium aluminate solution and treating the solution by illumination with pulsed near infrared light wave energy, spatially and temporally overlapped inside the solution, so as to produce a photo-induced nucleation of purified gibbsite crystals, without the need for external seed.

More specifically, Blanks '325 discloses a laser induced precipitation process for forming known alumina hydrate products. It does not disclose or claim, or even discuss, the formation of different polymorphs. It merely discloses a method for obtaining a known alumina hydrate for use in a conventional alumina purification process. As discussed above, a polymorph generally is defined as any of the crystalline forms of a substance capable of having different crystalline structures. Blanks '325 does not disclose whether a specific polymorph of alumina hydrate is desired and, more importantly, whether a different polymorph of alumina hydrate that is not typically created for use in the purification process (or an unknown polymorph of alumina hydrate) is created.

Blanks '325 merely discloses precipitating alumina hydrate for purification employing a laser treatment process properly to introduce infrared light into green Bayer liquor, e.g., such as by way of example from the first source facility, to provide enhancements in alumina yield of as much as 50 grams/liter without the addition of seed. While gibbsite may be the preferred form of alumina hydrate (whether for purification or for economic reasons) mentioned in Blanks '325, this apparently is a preferred form throughout the industry. Gibbsite Al(OH)$_3$ is a valuable and desirable mineral found in bauxite. This, coupled with the lack of disclosure on how to prepare different polymorphs, and polymorphs that normally would not result under the same conditions without the use of the selected light, indicates that Blanks '325 does not contemplate the present invention.

The mechanism by which the Blanks '325 method works also is different than that of the present patent application. Blanks '325 discloses that the laser removes undesirable organic compounds that are generally considered as inhibitors to alumina hydrate precipitation. In other words, the laser works by photochemically destroying organic impurities, thus permanently changing the conditions (i.e., with inhibitors removed) under which the nucleation proceeds. The method therefore requires that the laser light be absorbed by organic impurities in the solution, so that in Blanks '325 the wavelength of the laser needs to be tuned to match the absorption bands of the organic impurities in their samples. One feature of Blanks '325 is that by absorbing near infrared light, they are able to induce the photochemistry needed to destroy their organic impurities. In contrast, the present invention preferably involves no light absorption by the sample.

The Blanks '325 preferred embodiment employs any laser, which may be mode-locked so to emit sub-nanosecond pulses of near infrared light at an energy level of about 500–700 milliwatts. Typical cw mode-locked lasers have repetition rates of about 100 MHz (100 million pulses/second). For the Blanks '325 preferred laser, this corresponds to an energy/pulse of about 5–7 nanojoules. This is a very different type of laser than a Q-switched laser with nanosecond pulses with energy/pulse of about 0.1 Joules. The Blanks '325 pulses have an energy per pulse about ten million times weaker than the Q-switched laser used in the example of the present invention, and the electric fields associated with Blanks '325 laser pulses several orders of magnitude weaker than the electric fields associated with the lasers used in the present invention. Using a laser like the one disclosed in Blanks '325 would not induce nucleation in the glycine of the present invention.

BRIEF SUMMARY OF THE INVENTION

Briefly, the present invention is a novel method for using polarization to control the formation of polymorphs from supersaturated solutions using non-photochemical laser-induced nucleation. This method has been proven using supersaturated aqueous solutions of glycine and of alanine, and is extendable to supersaturated solutions of other systems. The polymorphs created with the present method have internal crystal structures that are different than those currently known or expected to form from selected substance in the absence of the wavelength of light selected. Surprisingly, the polymorphs can be created without chemically affecting or influencing the solution (that is, changing the chemistry of the solution). In effect, the present method is a non-chemical method of affecting the solution in a manner different than the prior art.

The internal structure of a crystal is referred to as polymorphism for substances and allotropism for elements. Polymorphic crystals are chemically identical but have different arrangements of atoms (or molecules) in the crystal lattice giving the solids different properties. Crystals of a given substance with different polymorphs have chemical and physical properties that vary. The fact that the solid properties can change makes different polymorphs behave differently when used for applications. For examples, a different polymorph of a dye would give a different color, and different polymorphs of drugs can have different bio-availability and dissolution properties. Much effort is spent in trying to find if a particular substance has additional polymorphs and in trying to prepare a particular polymorph.

This invention makes use of high-intensity pulses of laser light to induce nucleation in a supersaturated solution of unknown and/or unexpected polymorphs. By subjecting supersaturated solutions to laser light, the onset of nucleation occurs. Depending on the system, macroscopic crystals form on a timescale of seconds (aqueous urea) to hours (aqueous glycine). The laser light used can be at near-infrared wavelengths, where many solutions are transparent, so that the interaction between laser and solution may not or may be minimally be absorption of light by molecules. More likely interactions involve responses of molecules to the electric field associated with the laser light, such as the optical Kerr effect (the field-induced alignment of molecules) or electrostriction (the field-induced movement of molecules into regions of high electric field). In each of these interactions, the electric field of the light polarizes a molecule, meaning that it applies forces to the electrons and nuclei that comprise the molecule, and induces transient changes in the charge distribution in the molecule. Whatever the interactions between light and molecule, they aid in the formation of an ordered cluster of molecules that goes on to grow into a crystal. The unexpected discovery disclosed herein is that by using this technique, a polymorph can be created of an unknown polymorphism or of a polymorphism that is unexpected under given conditions. The laser-induced changes in molecular charge distribution can temporarily change the interactions between the molecules in a cluster, thereby changing the relative stability of different polymorphs.

Under a defined set of conditions, specific polymorphs will be present in a solution and will be known and expected by the person of ordinary skill in the art. More specifically, a variation in the defined conditions can change the expected and known polymorph. The present method can be used to prepare different polymorphs of substances that would not ordinarily be observed or occur, or to prepare polymorphs that are different from those that normally occur under given conditions in the absence of the instant method.

An object of this invention generally is the use of laser light to induce the nucleation of a polymorph from a supersaturated solution that is different from the polymorph that would spontaneously nucleate from the supersaturated solution under the same general conditions, but in the absence of the selected laser light.

Another object of this invention is the use of continuous wave or pulsed lasers, in various polarization states (e.g., plane-polarized versus circularly polarized), at various wavelengths where the supersaturated solution does not absorb, at various laser powers, pulse lengths, pulse repetition rates and exposure times, to induce the nucleation of a polymorph from a supersaturated solution that is different from the polymorph that would spontaneously nucleate from the supersaturated solution under the same general conditions, but in the absence of the selected laser light.

Another object of this invention is the use of various different process conditions (i.e., at various temperatures depending on the solubility of the compound being subjected to the light, various aging times, various supersaturation levels; various methods of achieving supersaturation such as cooling, heating, solvent evaporation, and changing solvent composition; and various different solvents such as organic or inorganic solvents) to induce the nucleation of a polymorph from a supersaturated solution that is different from the polymorph that would spontaneously nucleate from the supersaturated solution under the same general conditions, but in the absence of the selected laser light.

Another object of this invention is to provide of method of inducing the spontaneous nucleation of a different polymorph in a solution under a set of conditions through the use of a laser light without changing the chemistry of the solution.

DETAILED DESCRIPTION OF A PREFERRED EMBODIMENT

Figure 1:
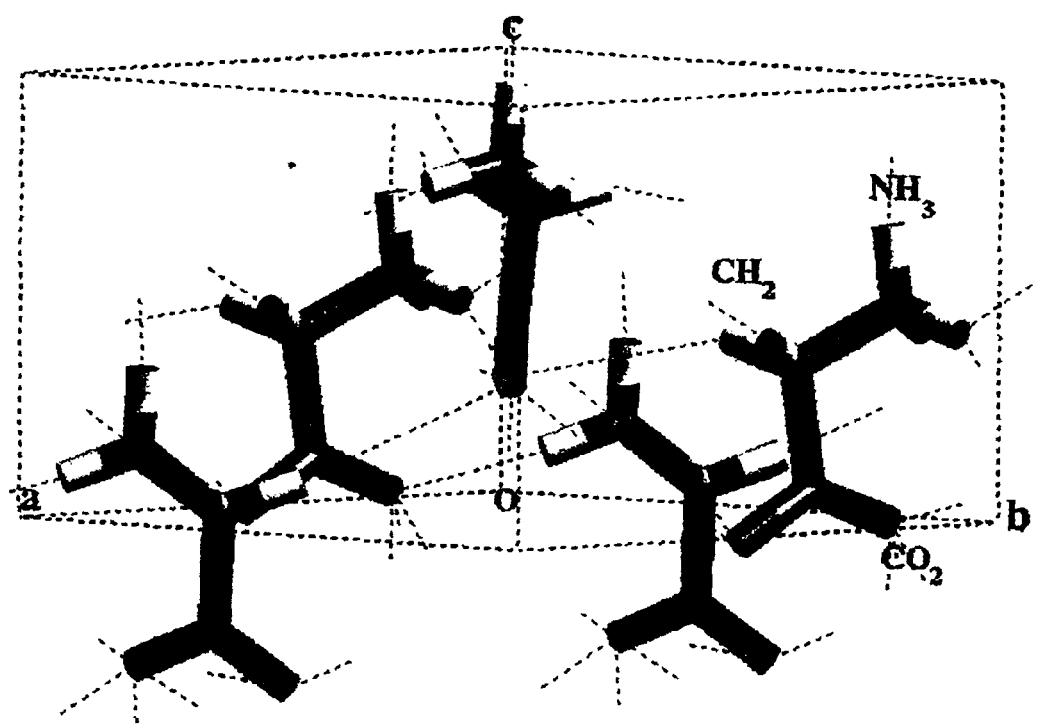
FIG. 1 is a representation of the crystal structure of alpha-glycine.

Nucleation in liquid solutions is a complex problem involving two components, and there appear to have been no other reports of light-induced nucleation from supersaturated solutions other than reported by inventors. Nevertheless, this problem is-of great theoretical and commercial importance, such as in industrial crystallization processes. The use of such a process to cause nucleation and crystal growth in such a way as to obtain a crystal structure of a desired size that would not normally form can be used to prepare different polymorphs of materials that have not been observed or to obtain a known polymorph under different conditions than those under which the polymorph is usually made.

The present invention is a novel method for creating different polymorphs of known substances. The novel polymorphs created with the present method have internal crystal structures that are different than those currently known or different than what would be expected by one of ordinary skill in the art without use of the present method. Surprisingly, the polymorphs can be created without chemically affecting or influencing the solution (that is, changing the chemistry of the solution). In effect, the present method is a non-chemical method of affecting the solution in a manner different than the prior art.

1. Use of Pulsed Laser Light to Induce Nucleation.

Pulses from a Q-switched Nd:YAG laser can induce nucleation in supersaturated solutions. In some cases, the crystallites that are formed have the same structure as crystallites that form when the same solution spontaneously nucleates. Such is the case with aqueous urea solutions with concentrations, c, in the range of 11.5–13.5M. These solutions were prepared by combining solid urea and water in 1.3-cm diameter Pyrex test tubes with screw-on caps. Great care was taken to exclude dust from samples. Supersaturated solutions were generated by heating the tubes to 45° C. and holding them at that temperature for several days. Once the urea was completely dissolved, the solutions were slowly cooled to room temperature. Solutions prepared in this way lasted for several weeks before spontaneously nucleating. At 25° C., the solubility of urea, $C_{sat}$, is 10.47M, so that the solutions had supersaturations, $c/c_{sat}$, ranging from 1.10 to 1.29.

After aging for one to two weeks, the solutions were illuminated with the 1.06-μm wavelength, plane-polarized output of a Quanta-ray DCR-1 Q-switched Nd:YAG laser. A portion of the doughnut-shaped beam with approximately constant intensity was selected by passing the beam through an aperture with an area of ~2 mm². With the laser oscillator alone, the measured energy per pulse was 0.02 J, while with the amplifier added, it was 0.1 J. The measured pulse width was 20 ns, and the pulse repetition rate was 10 pps. The unamplified and amplified pulses thus had intensities of 50 and 250 MW/cm², respectively.

Tests tubes containing the aged solutions were placed in the path of the laser beam. The curvature of the test tube walls caused some additional focusing of the laser beams, so that the solution was subjected to intensities somewhat higher that those listed in the previous paragraph. Exposure of the aged solutions to laser pulses from the oscillator alone was not sufficient to induce nucleation. With the amplifier added, nucleation typically occurred within 10–20 s. The onset of nucleation was observed visually by the formation of a needle-shaped crystallite. Shortly thereafter (within tens of seconds), the sample was filled with a complex polycrystalline mass. Crystallization could be induced with a single pulse or a train of pulses lasting from approximately 0.1 second to approximately 1 hour.

The urea solutions studied are highly transparent at the laser wavelength of 1.06 μm, so that photochemical effects are improbable. Therefore, the most likely candidates for laser-solution interactions are electric-field effects, such as the optical Kerr effect or electrostriction. The applied electric field apparently aids in organizing existing prenucleating clusters, increasing the chances that one will nucleate and grow.

2. Creation of Polymorphs.

Although it is known that a laser can induce some solutions to crystallize into the usual polymorph, as was the case with the urea-water system, it is disclosed for the first time that a laser, which is essentially not absorbed by the solution, can induce solutions to crystallize into a polymorph not normally known and/or expected by the person of ordinary skill in the art. This effect, disclosed and claimed herein, allows the preparation of different polymorphs of materials that have not been observed, or of known polymorphs under conditions different than those in which they are usually made. It is essential to note that the present invention creates different polymorphs (having a different internal crystal structure) and not known substances of different morphology (external crystal shape or appearance).

For example, such was the case with aqueous solutions of the amino acid glycine. Glycine is known to form at least three different polymorphs under different conditions. The one that normally forms from neutral aqueous solution is called the alpha form. Another form, known as the gamma form, forms from acidic or basic aqueous solutions. Whether the laser is pulsed through neutral solution, acidic or basic solution, the gamma form is produced.

Another example arises with aqueous solutions of the amino acid L-alanine. L-alanine is known to have only one polymorph. Subjecting an aqueous L-alanine solution to the laser resulted in an unexpected and unknown polymorph. The unknown and unexpected L-alanine was verified with x-ray diffraction, which produced a strong signal at 19.98, which is not known to occur in L-alanine solutions.

When light is incident on a molecule, the oscillating electric field of the light wave induces an oscillating electric dipole in the molecule. If several molecules are close to each other, these induced dipoles can interact resulting in either an increase or decrease in the attraction between adjacent molecules. This change in interaction energy can result in a change in the lowest-energy arrangement of molecules in a crystal, so that what was the lowest energy polymorph in the absence of light might not be the lowest energy polymorph in the presence of light. Thus, a polymorph that normally does not form under certain conditions could be induced to form in the presence of light. It is observed that the more intense the light, the stronger the associated electric field, and the greater the change in energy of the interacting molecules. One of the best sources of intense light is a high-power pulsed laser.

3. Experimental.

Supersaturated glycine solutions with concentrations ranging from 3.7–3.9M were prepared using the procedure described above for urea, with the exception that the glycine solutions were generated by heating to 50° C. Generally, glycine is added to a solvent such as water in an amount and under conditions so as to create a supersaturated solution of glycine in water. It should be noted that this experimental procedure is applicable to solutions other than glycine in water. Those of ordinary skill in the art can produce other supersaturated solutions of compounds in appropriate solvents without undue experimentation.

For example purposes only, suitable compounds include, but are not limited to, pharmaceuticals, amino acids, peptides, proteins, carbohydrates, amines, alkanes, alkenes, alkynes, aromatics, heterocyclic compounds, alcohols, organometallics, carboxylic acids, and derivatives of these compounds. Also for example purpose only, suitable solvents include, but are not limited to, organic, inorganic, and supercritical solvents. Once a compound is selected for laser treatment, the appropriate solvent is selected. Those of ordinary skill in the art can determine the appropriate solvent for a selected compound without undue experimentation.

When test tubes containing aged, supersaturated solutions of aqueous glycine were illuminated with 1.06 µm wavelength high-power laser pulses for several minutes, no changes were visually apparent. However, after several hours, one or two small approximately cubic crystals were observed to be growing at the bottom of the test tube. After a day or two, these crystals had grown to a size of about 10 mm$^3$. These crystals were removed from the solution and dried. Their structure was analyzed by grinding up the crystal into a powder, and obtaining an x-ray powder diffraction pattern. The x-ray peaks obtained matched those of the gamma-polymorph of glycine, plus a small percentage of the alpha-polymorph. When the same analysis is carried out on control crystals formed when identical solutions are allowed to spontaneously nucleate, only the alpha-polymorph is observed, thus supporting the premise of this invention. It has been found that suitable laser illumination times are from approximately 0.1 second to approximately 1 hour using a laser operating at 10 pulses per second.

Figure 2:
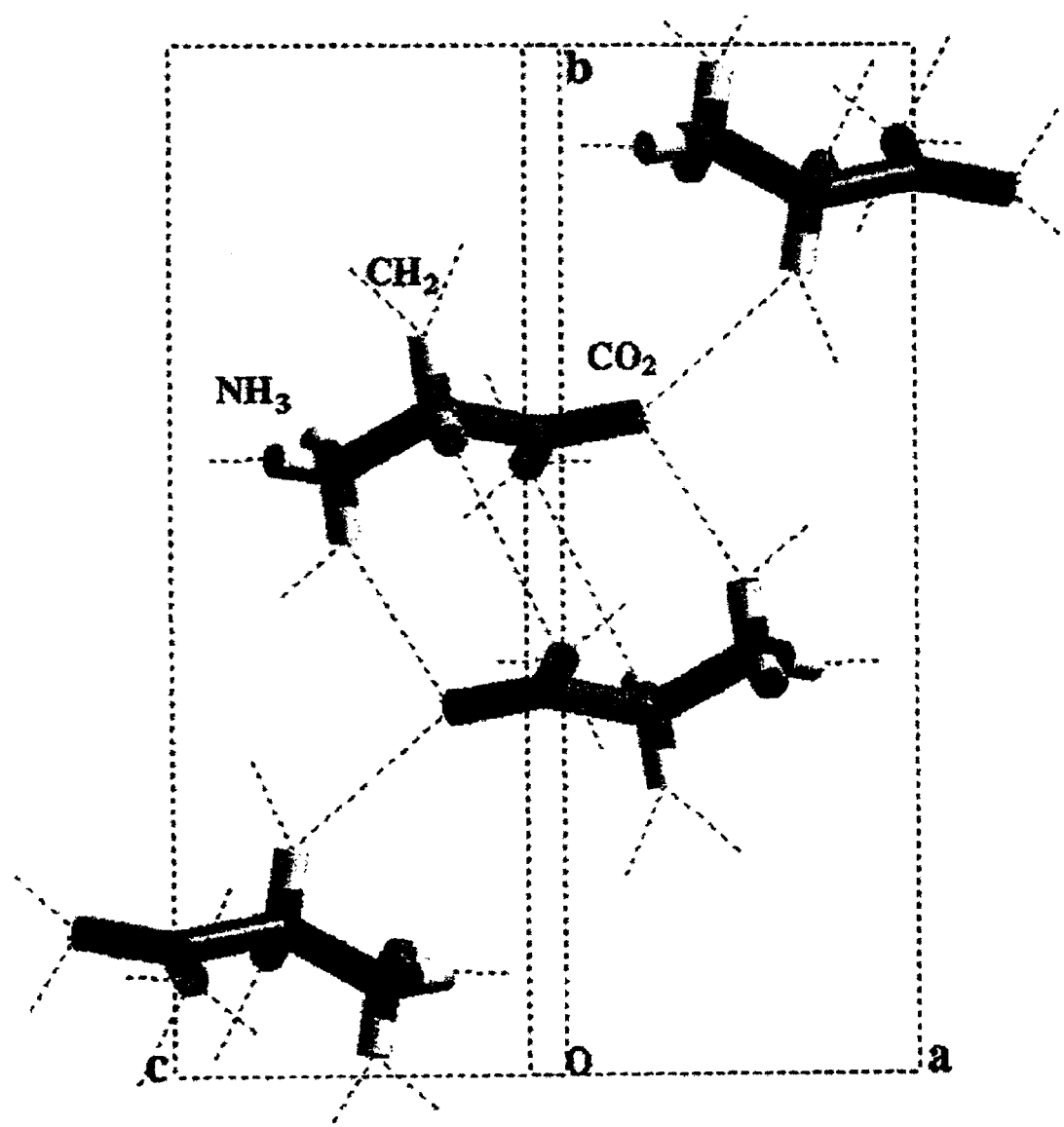
FIG. 2 is a representation of the crystal structure of gamma-glycine.
Figure 3:
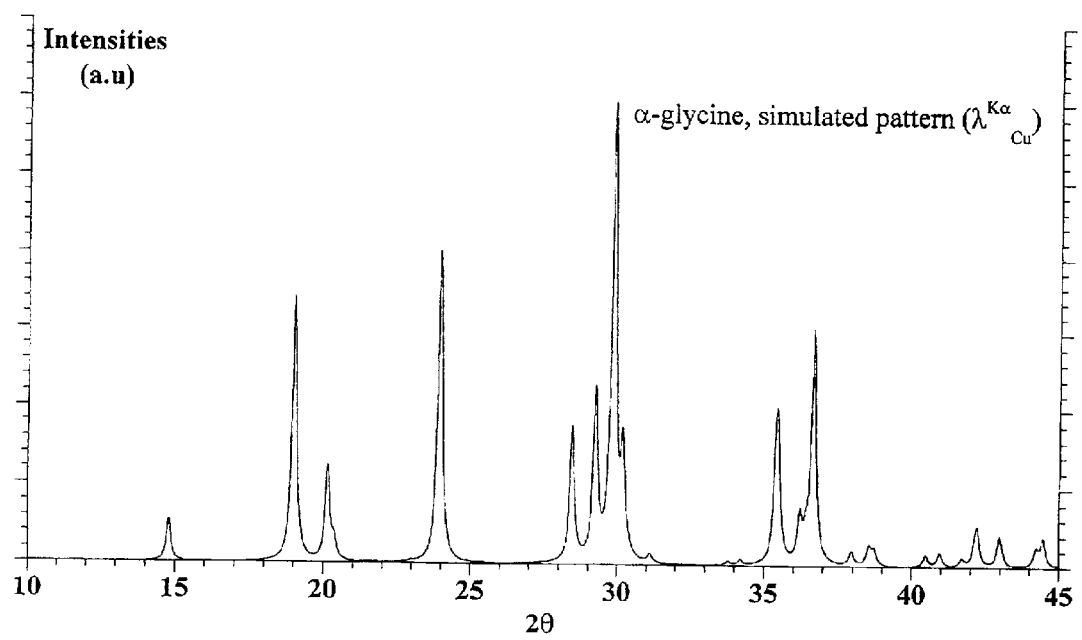
FIG. 3 is the x-ray diffraction pattern for alpha-glycine.
Figure 4:
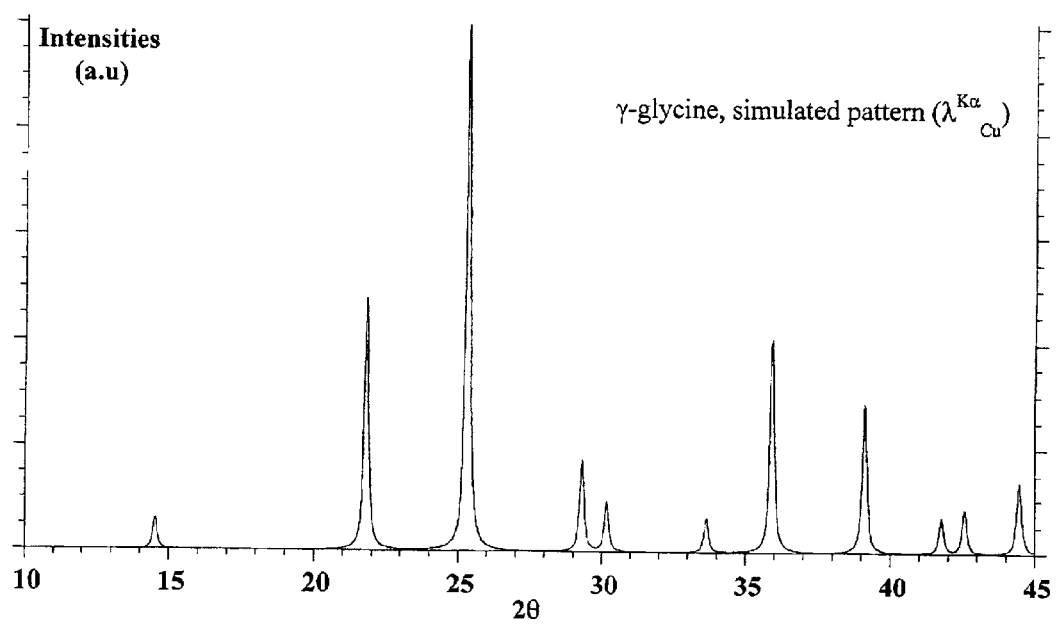
FIG. 4 is the x-ray diffraction pattern for gamma-glycine.
Figure 5:
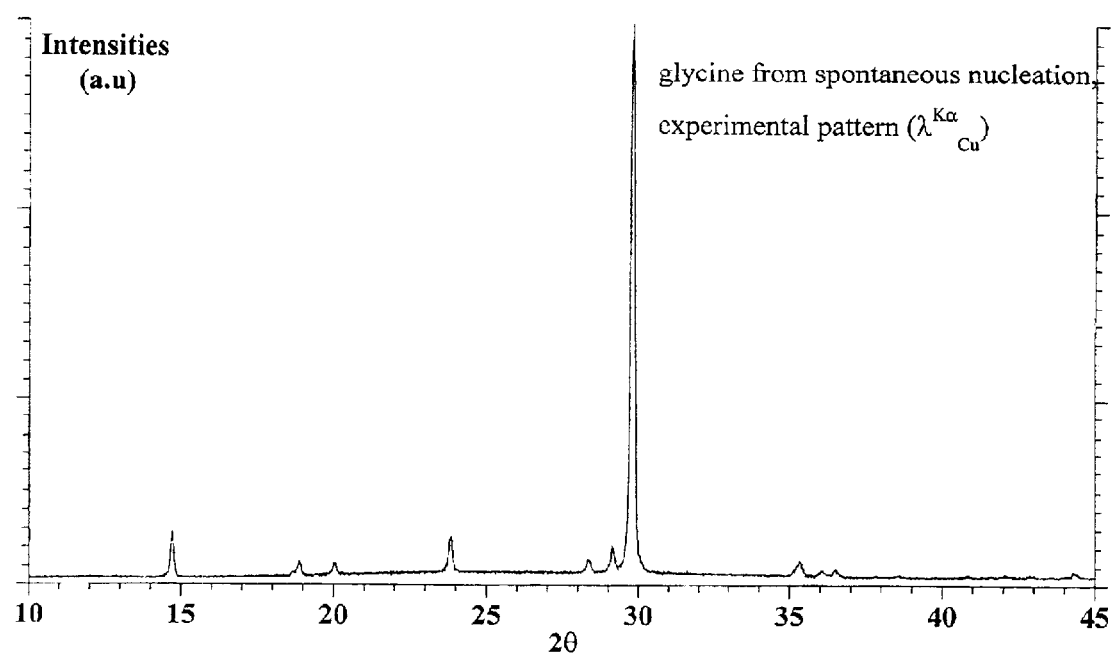
FIG. 5 is the x-ray diffraction pattern for glycine obtained from the spontaneous nucleation of a supersaturated aqueous glycine solution.
Figure 6:
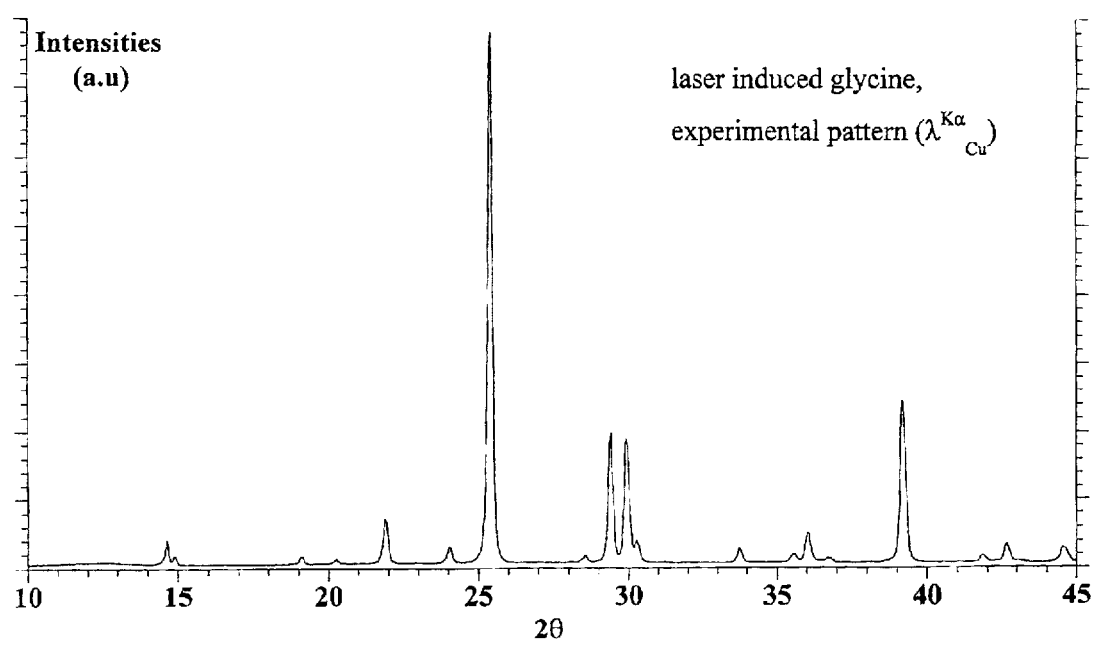
FIG. 6 is the x-ray diffraction pattern for glycine from the laser induced nucleation of the present invention of supersaturated solutions.

FIG. 1 shows a representation of the known crystal structure of alpha-glycine. FIG. 2 shows a representation of the known crystal structure of gamma-glycine. FIG. 3 is the known x-ray diffraction pattern for alpha-glycine. FIG. 4 is the known diffraction pattern for gamma-glycine. FIG. 5 is the x-ray diffraction pattern obtained from the spontaneous nucleation experiment discussed above. FIG. 6 is the x-ray diffraction pattern from the laser-induced nucleation experiment discussed above.

When aged supersaturated solutions of glycine are allowed to spontaneously nucleate, alpha glycine is the polymorph that occurs and is observed. In the experiment discussed above, the control crystals, obtained from the test tube containing the glycine that was allowed to spontaneously nucleate, were ground into a powder. FIG. 5 is the x-ray diffraction pattern obtained from these control crystals. As can be seen, the x-ray diffraction pattern of FIG. 5 indicates the presence of alpha-glycine and no gamma-glycine. In the experiment discussed above, the crystals obtained from the test tube containing the glycine that was illuminated with laser light were ground into a powder. FIG. 6 is the x-ray diffraction pattern obtained from these crystals. As can be seen, the x-ray diffraction pattern for FIG. 6 indicates the presence of gamma-glycine and a small percentage of alpha-glycine.

This invention makes use of pulsed, polarized laser light to induce nucleation in a supersaturated solution, as generally described in the inventors' listed publication, which is incorporated herein by this reference. The unexpected discovery is that by using this technique in some systems, a polymorph appears that would normally not appear without the use of the nonabsorbed laser. This method could therefore be used to prepare different polymorphs of materials, which have not been observed, or to obtain a known polymorph under different conditions than those in which it is usually made.

In the case of L-alanine, supersaturated L-alanine with concentration of 40% was prepared using the procedure described above for urea, and aged for 5 days. Nucleation was induced by short pulses from the laser such as described above. Visible crystals were produced of a bipyramidal appearance in times ranging from 10 to 60 minutes. The x-ray diffraction pattern was observed to have an intense signal in at 19.98 (2Θ), which is absent from the x-ray diffraction pattern of the known form of L-alanine polymorphism. Hence, a crystal of unknown and unexpected polymorphism was created by this method. The complete powder x-ray diffraction analysis for this example is:

| 2Θ | Intensity |
|---|---|
| 14.32 | 3.5013 |
| 16.30 | 9.066 |
| 19.98 | 100 |
| 20.40 | 13.67 |
| 20.58 | 11.49 |
| 21.94 | 12.526 |
| 26.12 | 58.669 |
| 26.66 | 7.2857 |
| 27.115 | 8.5958 |
| 28.86 | 17.26 |
| 28.92 | 11.175 |
| 31.48 | 35.848 |
| 32.06 | 4.9252 |
| 32.26 | 5.8888 |
| 32.34 | 5.9162 |
| 38.38 | 3.9167 |
| 38.46 | 4.2637 |
| 40.62 | 7.797 |
| 42.04 | 3.3918 |

This x-ray pattern is not the same pattern reported for the single known crystal form of L-alanine.

It should be noted that this experimental procedure is applicable to solutions other than alanine in water. Those of ordinary skill in the art can produce other supersaturated solutions of compounds in appropriate solvents without undue experimentation.

The above description sets forth the best mode of the invention as known to the inventors at this time, and is for illustrative purposes only, as it is obvious to one skilled in the art to make modifications to this process without departing from the spirit and scope of the invention and its equivalents as set forth in the appended claims. The use of glycine and L-alanine for the experimental portion of this specification is for illustrative purposes only, as it is clear to one of ordinary skill in the art that the procedure and results disclosed and claimed in this specification can be performed for other compounds with polymorphs without undue experimentation.

What is claimed is:

1. A method of producing crystal polymorph product of a substance selected from the group consisting of pharmaceuticals, amino acids, peptides, proteins, carbohydrates, amines, alkanes, alkenes, alkynes, aromatics, heterocyclic compounds, alcohols, organometallics. and carboxylic acids, comprising the steps of:
   a. preparing an aqueous solution of the selected substance;
   b. supersaturating the aqueous solution of the selected substance by a method selected from the group consisting of cooling, heating, sokent evaporation, and altering solvent composition;
   c. subjecting the supersaturated aqueous solution of the selected substance to a wavelength of laser light that is not absorbed by the supersaturated solution for a period of time so as to induce nucleation of at least one crystal of said polymorph;
   wherein said supersaturated aqueous solution is not affected chemically by the selected wavelength of light, said polymorph is different than the polymorphs that would nucleate in the absence of the wavelength of laser light selected, and the substance is not urea.

2. The method as claimed in claim 1, wherein the laser light is a laser beam that is pulsed.

3. The method as claimed in claim 2, wherein the laser beam pulses at 10 pulses per second.

4. The method as claimed in claim 3, wherein the supersaturated aqueous solution is subjected to the laser beam for a period of between 0.1 second and 1 hour.

5. The method as claimed in claim 4, wherein the laser beam is in the near infrared wavelengths.

6. The method as claimed in claim 5, wherein the laser beam is a high intensity laser beam.

* * * * *

UNITED STATES PATENT AND TRADEMARK OFFICE
CERTIFICATE OF CORRECTION

PATENT NO. : 7,122,642 B2  Page 1 of 1
APPLICATION NO. : 10/056490
DATED : October 17, 2006
INVENTOR(S) : Myerson It is certified that error appears in the above-identified patent and that said Letters Patent is hereby corrected as shown below:

| Col | Line | Correction |
| --- | --- | --- |
| 3 | 62 | "adicle" should be --article-- |
| 4 | 3 | "electrio" should be --electric-- |
| 5 | 54 | "from selected" should be --from the selected-- |
| 6 | 17 | "minimally be" should be --minimal-- |
| 7 | 36 | "is-of" should be --is of-- |
| 7 | 39 | "size" should be --type-- |
| 8 | 4 | "C" should be --c-- |
| 9 | 2 | "L-alanine solutions" should be --known L-alanine polymorphs-- |
| 12 | 1 | "sokent" should be --solvent-- |

Signed and Sealed this

Thirteenth Day of February, 2007

JON W. DUDAS
*Director of the United States Patent and Trademark Office*